(12) United States Patent
Wilson

(10) Patent No.: US 7,039,547 B2
(45) Date of Patent: May 2, 2006

(54) METHOD AND APPARATUS FOR LOCALIZING BIOMAGNETIC SIGNALS

(75) Inventor: Harold Wilson, Port Moody (CA)

(73) Assignee: VSM Medtech Systems Inc., Coquitlam (CA)

( * ) Notice: Subject to any disclaimer, the term of this patent is extended or adjusted under 35 U.S.C. 154(b) by 159 days.

(21) Appl. No.: 10/798,252

(22) Filed: Mar. 12, 2004

(65) Prior Publication Data

US 2005/0203713 A1     Sep. 15, 2005

(51) Int. Cl.
*G06F 19/00* (2006.01)
(52) U.S. Cl. ...................... 702/150; 324/260
(58) Field of Classification Search ............... 702/74, 702/36, 38, 69, 77, 150, 152, 159, 188, 195; 324/200, 246, 252, 260
See application file for complete search history.

(56) References Cited

U.S. PATENT DOCUMENTS

2005/0150697 A1* 7/2005 Altman et al. ........... 178/19.02

OTHER PUBLICATIONS

J.S. Bendat and A.G. Piersol, *Random Data: Analysis and Measurement Procedures*; Wiley-Interscience 1971.

K. Uutela and M. Hamalainen; *Correcting for head movements in MEG inverse problem*; Proc. 12th Int. Conf. on Biomagnetism, pp809-812, Aug. 2000.

J.C. de Munck, J.P.A. Verbunt, D. Van't Ent and B.W. Van Dijk; *The use of an MEG device as 3D digitizer and motion-monitoring system*; Phys. Med. Biol. v.46 (2001) pp2041-2052.

K. Uutela, S. Taulu, and M. Hamalainen; *Detecting and Correcting for Head Movements in Neuromagnetic Measurements*; NueroImage v. 14 (2001) pp 1424-1431.

* cited by examiner

*Primary Examiner*—Edward Raymond
(74) *Attorney, Agent, or Firm*—Oyen Wiggs Green & Mutala LLP

(57) ABSTRACT

A method for locating an object relative to an array of magnetic sensors in an environment in which there is present a noise signal having a fundamental frequency $f_{NOISE}$, includes generating one or more magnetic signals by means of one or more magnetic emitters mounted at known locations on the object during an integration time T. The one or more magnetic signals have one or more frequencies. The one or more magnetic signals and the noise signal are detected at six or more magnetic detectors. Relative amplitudes of the magnetic signals are determined. The one or more frequencies of the magnetic signals are substantially equal to frequencies at which a power spectrum of the detected noise signal has zeros.

38 Claims, 2 Drawing Sheets

METHOD AND APPARATUS FOR LOCALIZING BIOMAGNETIC SIGNALS

TECHNICAL FIELD

The invention relates to the measurement of magnetic fields generated by biological activity (biomagnetic signals). The invention has application to the localization of sources in magnetic imaging of biological structures. Some embodiments of the invention are used to provide continuous head localization information in magnetoencephalography.

BACKGROUND

Magnetoencephalography ("MEG") involves detecting magnetic fields produced within a subject's brain. Information about such biomagnetic fields is most useful when it can be associated with particular structures within the subject's brain. One can localize the subject's head relative to the measured magnetic fields. To do this, the position of the subject's head relative to the magnetic detectors used to detect the magnetic fields must be known.

One way to localize a subject's head is to attach small coils at three or more known locations on the subject's head. The coils create fluctuating magnetic fields when alternating electrical currents are passed through them. Magnetic detectors are used to detect the coils' magnetic fields. The location of the coils, and thus the location of the subject's head, can be determined from the detected magnetic fields of the coils.

One problem with some current head localization systems is that the coils generate large magnetic fields that can saturate the very sensitive magnetic field detectors used to detect biomagnetic signals. Because of this, head localization cannot be performed while biomagnetic signals are being measured. With such current systems it is necessary to perform head localization before and/or after acquiring data about the biomagnetic signals. Such systems assume that the position of the subject's head changes predictably and can be determined from its positions before and/or after the biomagnetic signals are measured. These assumptions are not always accurate.

Acquiring biomagnetic signals is often performed over significant time spans. During these times a subject's head is likely to move even if the subject is attempting to stay still.

Magnetic noise can exacerbate the problems with head localization. The magnetic detectors used to detect the magnetic fields from the coils will also pick up noise signals, such as signals at the power line frequency (generally 60 Hz in North America and 50 Hz in Europe) and at harmonics of the powerline frequency. Such noise signals can degrade the accuracy with which the positions of each of the coils can be determined. Magnetic noise includes environmental background noise, noise resulting from operation of the magnetic detectors and other components in the signals from the magnetic detectors which do not arise from the magnetic fields of the coils.

There is a need for systems which permit continuous localization of heads and other structures during the acquisition of biomagnetic signals. There is a particular need for such systems which are relatively insensitive to noise.

SUMMARY OF THE INVENTION

This invention relates to localizing sources of biomagnetic signals. One aspect of the invention provides a method for locating an object relative to an array of magnetic sensors in an environment in which there is present a noise signal having a fundamental frequency $f_{NOISE}$, the method comprising generating one or more magnetic signals by means of one or more magnetic emitters mounted at known locations on the object, the one or more magnetic signals having one or more frequencies; during an integration time T, detecting the one or more magnetic signals and the noise signal at six or more magnetic detectors; and, determining relative amplitudes of the magnetic signals; wherein the one or more frequencies of the magnetic signals are substantially equal to frequencies at which a power spectrum of the detected noise signal has zeros.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
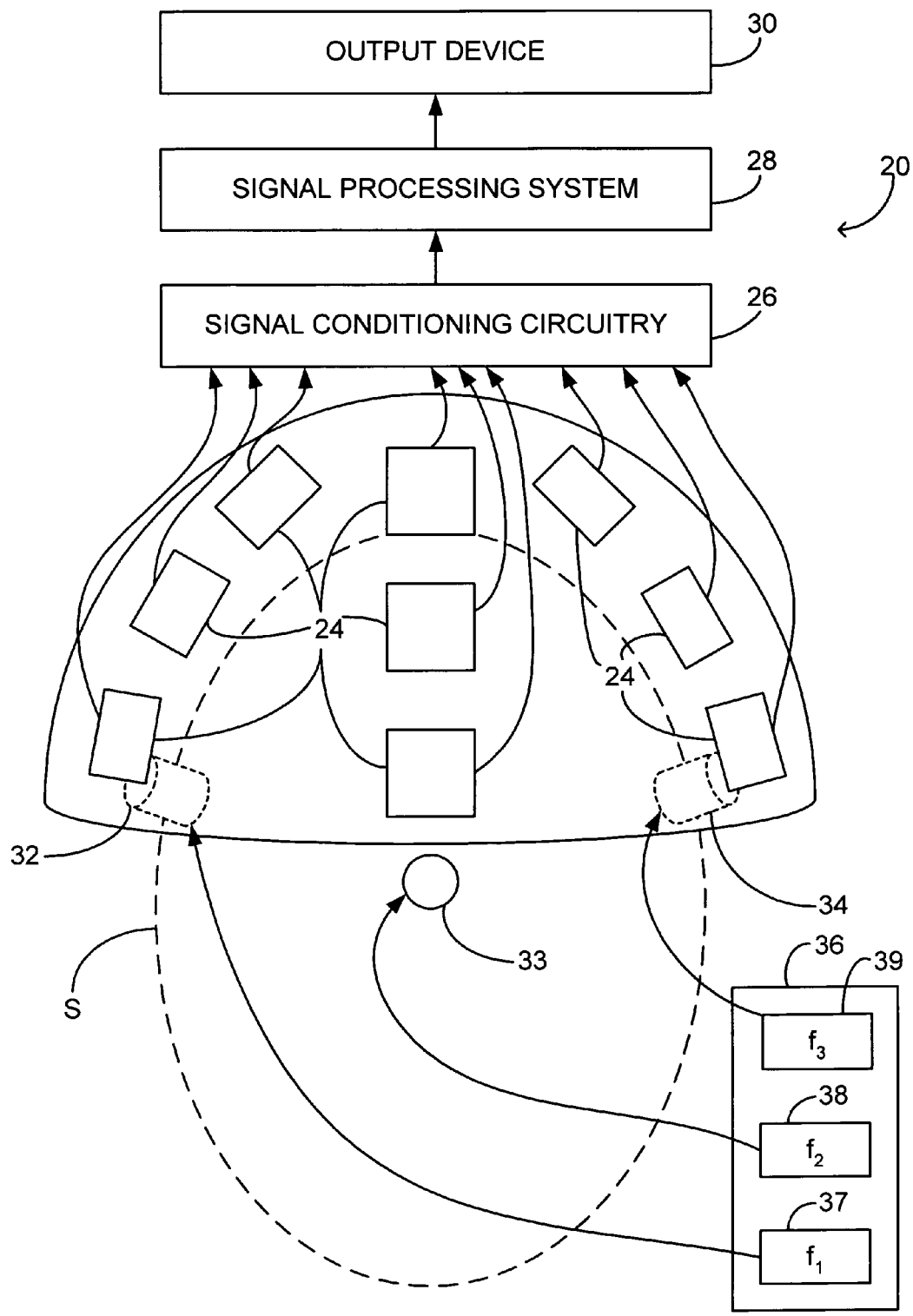
FIG. 1 is a schematic diagram of a MEG system which performs head localization according to one embodiment of the invention; and, FIG. 2 is a flow chart which illustrates a method for locating an object relative to an array of magnetic sensors according to another embodiment of the invention.

FIG. 1 shows a MEG system 20 according to one embodiment of the invention. System 20 includes a number M of magnetic detectors 24 which are located to detect magnetic fields originating within the head of a subject S. While FIG. 1 represents a detector array by only a few detectors 24, a MEG system typically has a few hundred detectors 24. Detectors 24 may be SQUID detectors. Signals from detectors 24 are appropriately conditioned by way of suitable signal conditioning circuitry 26. The processed signals are provided to a signal processing system 28. Signal processing system 28 generates output at an output device 30. The output may comprise, for example, a graphical display, a data file containing MEG data, or the like.

Coils 32, 33 and 34 are attached to the subject's head and are respectively driven with signals of frequencies $f_1$, $f_2$ and $f_3$ (collectively referred to as $f_q$) by a controller 36 which, in the illustrated embodiment includes oscillators 37, 38, and 39. Driving signals for coils 32, 33 and 34 may be obtained in any suitable manner.

The location of any one of coils 32, 33 and 34 can be determined in standard ways if the amplitudes of the magnetic signals produced by the coil at a sufficient number of detectors 24 is known. This invention provides a novel noise-insensitive mechanism for finding these amplitudes. The detectors 24 used for locating the coils may be the same detectors used to obtain MEG data. The detectors may be used simultaneously to obtain MEG data and to obtain information used to locate the coils.

Detectors 24 are sampled periodically to provide a sequence of samples. The sequence of samples is acquired at a sampling rate sufficient to detect the signals from the coils. The sampling frequency is typically at least twice, and preferably at least four times the highest coil frequency. Sampling is performed during an integration time, T. The integration time T is selected so the signals from the coils 32, 33, 34 can be separated from each other and from background noise. Ideally, when the output of detectors 24 is integrated over the integration time, signals at the noise frequency will integrate to zero over the integration time. The integration time is selected based upon the expected frequency of noise.

Since the position of a subject's head must be updated frequently, the integration time must be short, and this results in "spectral leakage" where the measurement of a head-coil signal at one frequency is affected by signals from the other head coils at other frequencies and/or by background noise. Spectral leakage can be reduced by multiplying the outputs of detectors 24 by a taper function in the integrations, and by selecting coil frequencies to be frequencies that do not interfere with each other.

Since the detectors are sampled over finite integration times, the locations of the zeros in the noise power spectrum depends upon the shape of the taper function, if any, applied to the samples. The examples discussed herein relate to the special case where the taper function is a "boxcar" (i.e. all of the samples in the integration time T are weighted equally) and the noise environment is dominated by signals at a single frequency $f_{NOISE}$ and its harmonics. The locations of the zeros will differ if other taper functions are used. If a taper function other than a boxcar is used then the coil frequencies may be selected to be at zeros of the power spectrum of the expected noise signal convolved with the taper function. The issue of separating signals and spectral leakage with finite integration times T is discussed in many signal-analysis references, for example "Random data: Analysis and Measurement Procedures" by J. S. Bendat and A. G. Piersol.

Figure 2:
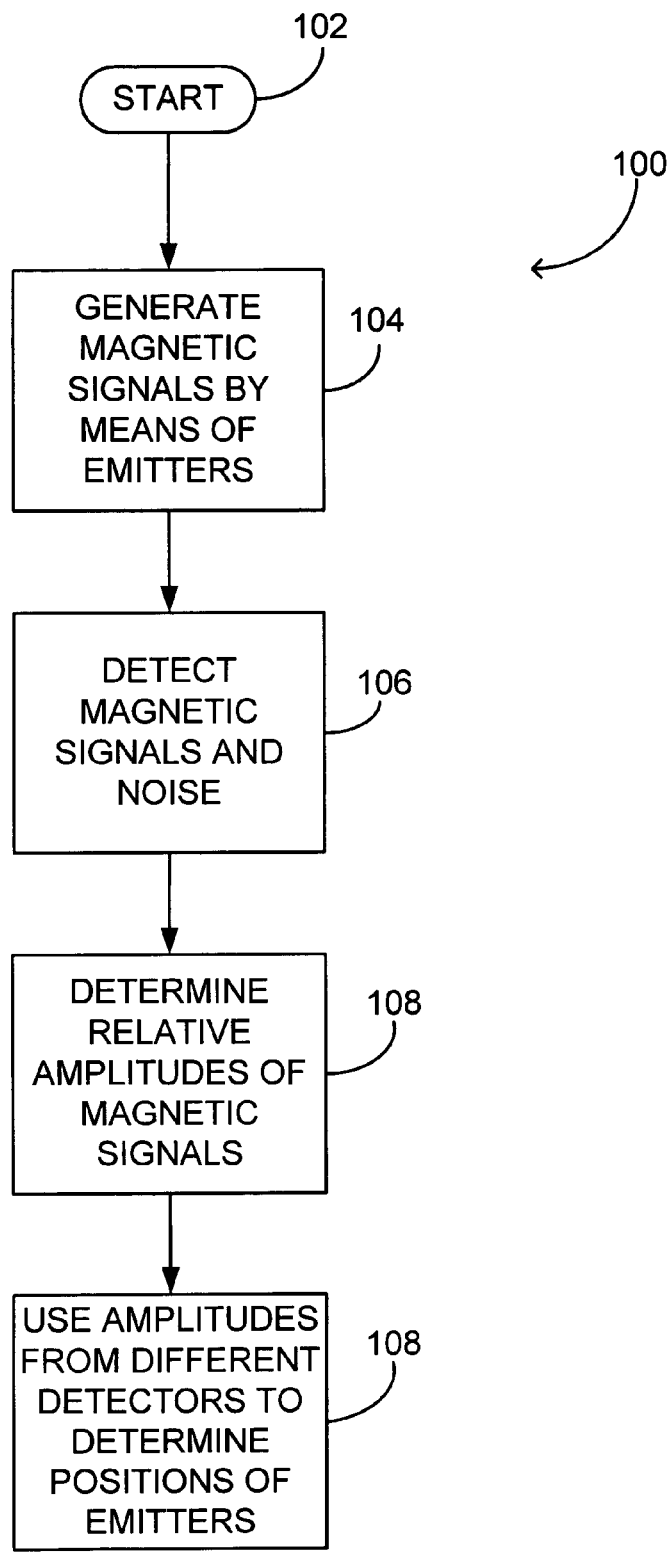

FIG. 2 is a flowchart illustrating a method 100 according to one embodiment of the invention. After method 100 begins at block 102, magnetic signals are generated at block 104. The magnetic signals are generated by means of magnetic emitters, which preferably comprise coils. At block 106, the magnetic signals and the noise are measured by detectors 24. At block 108, the relative amplitudes of the magnetic signals are determined, as described further below.

Where the frequency of the noise signal is $f_{NOISE}$, and a boxcar taper function is used, then suitable integration times T satisfy the formula:

$$T = \frac{N_1}{f_{NOISE}} \quad (1)$$

where $N_1$ is an integer and $N_1 \geq 2$. For example, if the noise fundamental frequency $f_{NOISE}$ is 60 Hz then the integration time may be selected to be $N_1/60$ seconds. If $N_1=4$ then an integration time of 1/15 second is used. If the noise fundamental frequency is 50 Hz then the integration time may be selected to be $N_1/50$ seconds. If $N_1=5$ an integration time of 1/10 second is used. The integration time is preferably chosen to be short relative to any likely motions of the subject's head.

The coil frequencies $f_1$, $f_2$ and $f_3$ are selected to be different from one another and at or near frequencies to which the noise fundamental frequency and its harmonics cannot spread, which are referred to herein as ideal coil frequencies $f_{qi}$. Ideally, each coil frequency $f_{qi}$ satisfies the formula:

$$f_{qi} = \frac{N_2}{T} = \frac{N_2 \times f_{NOISE}}{N_1} \quad (2)$$

Where $N_2$ is an integer that is not a multiple of $N_1$. For example, where the noise fundamental frequency is 60 Hz and $N_1=2$ then Equation (2) yields frequencies 30 Hz, 90 Hz, 150 Hz, 210 Hz . . . etc. In preferred embodiments, the coil frequencies are chosen so that they will not interfere with MEG measurements being made. It is also desirable to maintain the coil frequencies low enough that currents induced in the subject by the fluctuating magnetic fields of the coils are too small to interfere significantly with the coil signals. For example, in some MEG studies, the MEG signals of interest have frequencies of about 10 Hz. In such cases, the coil frequencies may be chosen to be sufficiently large that the lowest coil frequency is significantly higher than the frequencies of MEG signals to be studied. Typically the coil frequencies are in the range of 25 Hz to 275 Hz. Higher coil frequencies could also be used.

As another example, if a user is interested in MEG signals having frequencies in the range of 70–330 Hz, the user could choose $N_1=8$ and $N_2=3, 5, 7$. This choice of $N_2$ yields coil frequencies of 22.5, 37.5 and 52.5 Hz. In this example, the user would need to filter power line noise signals (including harmonics) which are within the range of frequencies of the MEG signals being studied.

The complex amplitude, $A_q^m$, of the signal from the $q^{th}$ coil at the $m^{th}$ detector 24 can be determined from the set of samples $S_k^m$ acquired over an integration period at the $m^{th}$ detector by computing the sum:

$$A_q^m \equiv \frac{2}{N_m} \left[ \sum_{k=0}^{N-1} I_{qm}^m S_k^m \cos(2\pi k f_q / f_s) - i \sum_{k=0}^{N-1} S_k^m \sin(2\pi k f_q / f_s) \right] \quad (3)$$

where $f_q$ is the frequency of the $q^{th}$ coil, $f_s$ is the detector sample rate, $N=Tf_s$ and k is an index indicating the order of the samples in the sequence of samples from each of the magnetic detectors. For locating the coils it is only necessary to obtain the relative amplitudes (including sign) of the signals from each coil at the different detectors (the complex phase of the signal from each coil is not important). A simple way to obtain the relative amplitudes of the signals is to use a detector which detects a strong signal (for example, the detector which detects the strongest signal) to establish the phase. If detector $m_0$ has the strongest signal at frequency $f_q$ then the real relative amplitudes of the signals can be given by:

$$R_q^m = \text{Re}\left(A_q^m \times \frac{|A_q^{m0}|}{A_q^{m0}}\right) \quad (4)$$

Equation (4) is sufficiently accurate as long as the coil signals detected by at least a few of detectors 24 are strong enough that noise does not cause significant errors in the phases of the detected signals. More sophisticated techniques for obtaining the relative real amplitudes of the coil signals could be used but are usually unnecessary. For example, a least squares best estimate of the phase, $\phi_q$, and relative real amplitude, $R_q^m$, of the coil signal of coil q could be obtained as follows:

$$\tan(2\phi_q) = \frac{2 \sum_m I_{qm} R_{qm}}{\sum_m (R_{qm}^2 - I_{qm}^2)} \quad (5)$$

and, $$R_q^m = \text{Re}((R_{qm} + i I_{qm}) e^{-i\phi_q}) \quad (6)$$

In some cases one or more of the frequencies $f_1$, $f_2$ and $f_3$ of the coil signals may not be exactly equal to the ideal frequencies $f_{qi}$ identified by Equation (2). This could occur, for example, if the circuits used to drive the coils provide limited choice of coil frequencies. In such cases one should still use the ideal frequencies $f_{qi}$ in Equation (3) and not the actual frequencies of the coil signals. To obtain the best accuracy in cases where the frequencies $f_1$, $f_2$ and $f_3$ of the coil signals are not exactly equal to the ideal frequencies identified by Equation (2) one should compensate for spectral leakage from the signals of the other coils.

In cases where one or more of the coil frequencies is not ideal, it is desirable that the actual frequencies of the coil signals be related to ideal frequencies of the coil signals by the following inequality:

$$\sqrt{(f_1 - f_{1i})^2 + (f_2 - f_{2i})^2 + (f_3 - f_{3i})^2} \leq \frac{1}{2T} \quad (7)$$

Where equation (7) is satisfied, the actual coil frequencies are "substantially equal" to the ideal coil frequencies. It can be seen that equation (7) will be satisfied if none of the coil frequencies departs from a corresponding ideal frequency by more than approximately $$\frac{0.3}{T}.$$

To compensate for spectral leakage that occurs when non-ideal coil frequencies are used, one can define the functions $G_C$ and $G_S$ as follows:

$$G_C(f_q, f_{qi}) = \frac{2}{T}\int_{-\frac{T}{2}}^{\frac{T}{2}} \cos(2\pi f_q t) e^{-i2\pi f_{qi} t} dt \quad (8)$$

$$= \frac{\sin(\pi(f_q - f_{qi})T)}{\pi(f_q - f_{qi})T} + \frac{\sin(\pi(f_q + f_{qi})T)}{\pi(f_q + f_{qi})T}$$

and, $$G_S(f_q, f_{qi}) = \frac{2i}{T}\int_{-\frac{T}{2}}^{\frac{T}{2}} \sin(2\pi f_q t) e^{-i2\pi f_{qi} t} dt \quad (9)$$

$$= \frac{\sin(\pi(f_q - f_{qi})T)}{\pi(f_q - f_{qi})T} - \frac{\sin(\pi(f_q + f_{qi})T)}{\pi(f_q + f_{qi})T}$$

where $f_{qi}$ is the ideal frequency closest to $f_q$. The real and imaginary parts $C_q$ and $S_q$ of the amplitudes measured at ideal frequencies $f_{qi}$ can be related to the real and imaginary parts $R_q$ and $I_q$ of the true head coil amplitudes by way of the matrix equations:

$$\begin{bmatrix} C_1 \\ C_2 \\ C_3 \end{bmatrix} = \begin{bmatrix} G_C(f_1, f_{1i}) & G_C(f_2, f_{1i}) & G_C(f_3, f_{1i}) \\ G_C(f_1, f_{2i}) & G_C(f_2, f_{2i}) & G_C(f_3, f_{2i}) \\ G_C(f_1, f_{3i}) & G_C(f_2, f_{3i}) & G_C(f_3, f_{3i}) \end{bmatrix} \times \begin{bmatrix} R_1 \\ R_2 \\ R_3 \end{bmatrix} \quad (10)$$

and, $$\begin{bmatrix} S_1 \\ S_2 \\ S_3 \end{bmatrix} = \begin{bmatrix} G_S(f_1, f_{1i}) & G_S(f_2, f_{1i}) & G_S(f_3, f_{1i}) \\ G_S(f_1, f_{2i}) & G_S(f_2, f_{2i}) & G_S(f_3, f_{2i}) \\ G_S(f_1, f_{3i}) & G_S(f_2, f_{3i}) & G_S(f_3, f_{3i}) \end{bmatrix} \times \begin{bmatrix} I_1 \\ I_2 \\ I_3 \end{bmatrix} \quad (11)$$

The simple form of equations (10) and (11) as a pair of 3×3 matrix equations can be achieved by expressing the integration time as the interval $-T/2 \leq t \leq T/2$. Equations (10) and (11) can be replaced with an equivalent single 6×6 matrix equation or an equivalent single 3×3 matrix equation in which the variables and coefficients have complex values. Equations (10) and (11), or their mathematical equivalents, may be applied to obtain corrected amplitudes to compensate for the coil frequencies not being exactly at the ideal frequencies described above.

Motion of the head coils will result in a time-varying signal amplitude, which in turn will cause spectral leakage such that the signal from one head coil affects the measurement of the amplitude of the signals from the other head coils, even if the coils are operated at the ideal frequencies specified in equation (2). Where the integration time is short enough that the signal amplitude can be modelled as a quadratic function, the spectral leakage can be considered to be a function of frequency separation only. Spectral leakage due to motion of the coils decreases with increased separation between the frequencies $f_1$, $f_2$ and $f_3$. It is desirable to maintain a spacing of, for example, 30 Hz or more, between all pairs of $f_1$, $f_2$ and $f_3$ to minimize spectral leakage.

It can be appreciated that selecting coil frequencies as described above is a special case of a more general method. In general, the coil frequencies are selected to be equal to or substantially equal to those frequencies at which the power spectrum of the noise signal is zero. In this context, "substantially equal" is defined in equation (7) above. Frequencies which are all within about $$\frac{0.3}{T},$$

where T is the integration time, of the corresponding ideal frequencies are substantially equal to the ideal frequencies. This is typically close enough to compensate for errors which arise from the coil signals not being at the ideal frequencies by using, for example, equations (10) and (11).

Standard techniques may be used to determine the locations of each of the coils based upon the amplitudes determined above. Some suitable head localization algorithms are described in de Munck et al., Phys. Med. Biol. 46 (2001) pp. 2041–2052. For example, one way to determine the positions of the coils can be used in the case in which the coils are each small enough to be considered a point source and the detectors are magnetometers or first order gradiometers.

It can be shown that the position $\vec{y}$ can be determined by finding a value for $\vec{y}$ which minimizes the function H where:

$$H(\vec{y}) = \sum_k \left(\vec{m}(\vec{y}) \cdot \vec{C}_k(\vec{y}) - s_k\right)^2 = \vec{m}\overset{\leftrightarrow}{A}\vec{m} - 2\vec{b}\cdot\vec{m} + \sum_k s_k^2 \quad (12)$$

where $\vec{m}(\vec{y})$ is the best-fit estimate of the source magnetic moment if the source is at point $\vec{y}$. It is related to matrix $\overset{\leftrightarrow}{A}$ and vector $\vec{b}$ by $\vec{m}(\vec{y}) = \overset{\leftrightarrow}{A}^{-1}\vec{b}$ Matrix $\overset{\leftrightarrow}{A}$ and vector $\vec{b}$ are functions of $\vec{y}$ and are defined below;

$S_k$ is the amplitude of a the signal from a coil in the $k^{th}$ detector;

$\vec{C}_{k\mu}(\vec{y})$ is the response of sensor k to a magnetic source located at point $\vec{y}$ with moment of unit strength and oriented in spatial direction $\mu$. $C_{k\mu}(\vec{y})$ may be represented as a power series in $\vec{y}$ and the parameters that describe sensor k, or it may be expressed as an analytic function of the same variables;

Matrix $\overleftrightarrow{A}$ is a function of source point $\vec{y}$. The components of $\overleftrightarrow{A}$ are $$A_{\mu\nu} = \sum_k C_{k\mu}(\vec{y}) C_{k\nu}(\vec{y}); \quad (5)$$

Vector $\vec{b}$ is a function of source point $\vec{y}$. The components of $\vec{b}$ are $$b_\nu = \sum_k s_k C_{k\nu}(\vec{y}). \quad (10)$$

It is not necessary to use the signals detected at all detectors to determine the locations of each of the coils. It is generally acceptable to use signals detected at a subset of the detectors. Acceptable results can generally be obtained using coil signals detected at 30 or fewer properly chosen detectors. In some embodiments of the invention coil signals from 12 to 15 detectors are used to determine the position of each coil. It is not necessary that the same subset of coils be used to determine the positions of all of the coils. Indeed, it is desirable to use a different subset of the detectors for determining the position of each of the coils. Since the coils are expected to be in positions which are roughly known one could establish a predetermined subset of detectors to use for each coil.

A subset of the magnetic detectors to use for determining the position of a coil may be identified in various ways. In general it is desirable to include in the subset detectors having outputs which vary strongly with the position of the coil relative to the detector. In some 5 embodiments of the invention multiple criteria are used to select detectors in the subset. For example, in some embodiments, some detectors are included in the subset because they have relatively large signals from the coil and other detectors are included in the subset because the coil signal that they detect has a large variation with coil position.

One algorithm for selecting detectors to include in the subset for a coil involves the following steps:

Determine a number $M_f$ of detectors to use for the fit. $M_f$ may be predetermined. $M_f$ in the range of 12 to 15 is generally sufficient. $M_f$ must be at least 6. More detectors may be required for coils which are relatively far from the closest detectors.

Sort the detectors in order of the amplitude of the signal detected from the coil. Select the $M_{f0}$ detectors having the largest signals for inclusion in the subset. $M_{f0}$ may be, for example, 2N/3. In general $M_{f0}$ may be any significant fraction of $M_f$ (i.e. a fraction greater than about ⅓N).

Calculate an indicator, V, of the variation in the signal with coil position for each detector and include in the subset the $M_f$-$M_{f0}$ detectors having the largest values of V. Various functions can be used as the indicator. For example, in some embodiments, V is given by:

$$V = \frac{|s_m - s_{max}|}{|\vec{r}_m - \vec{r}_{max}|} \quad (13)$$

where $S_{max}$ is the amplitude of the signal at the detector having the largest signal from the coil and $\vec{r}_{max}$ is the location of the detector having the largest signal from the coil.

Information about the coil positions may be used in various ways. For example, the coil positions may be monitored in real time and compared to reference positions. Suitable action may be taken based upon the coil positions. For example:

an alarm may be triggered if the coil positions are determined to be too far away from the reference positions;

data may be discarded for those times during which the coil positions are determined to be too far away from the reference positions;

a sensory (e.g. visual, audible or tactile) feedback indicator may be provided to help subjects keep their heads in a desired position;

the positions of the coils may be recorded along with MEG data for later correction of the MEG data to account for motion of the subject's head;

the MEG data may be corrected in real time to correct for motions of the subject's head. One way to correct the MEG data is described in the co-pending commonly owned patent application entitled MOTION COMPENSATION IN BIOMAGNETIC MEASUREMENT being filed together herewith, which is hereby incorporated by reference herein.

Certain implementations of the invention comprise computer processors which execute software instructions which cause the processors to perform a method of the invention. For example, one or more processors in a controller for a MEG system may implement a method of FIG. 2 by executing software instructions from a program memory accessible to the processor(s). The invention may also be provided in the form of a program product. The program product may comprise any medium which carries a set of computer-readable signals comprising instructions which, when executed by a computer processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like or transmission-type media such as digital or analog communication links.

Where a component (e.g. a software module, processor, detector, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

In the above description, a number of coil signals are monitored simultaneously. In alternative embodiments of the invention the coil signals are time multiplexed. In this case, the coil signals may be at the same frequency or at different frequencies. The coil frequency or frequencies are chosen to be frequencies at which the power spectrum of the expected noise signal convolved with any taper function being applied has zeros.

The foregoing discussion assumes that the magnetic signals generated by the coils are each at a single fixed frequency and remain uniform in frequency and amplitude over the integration period. In general, this is not necessary.

Magnetic detectors 24 may be of any suitable types. For example, detectors 24 could be magnetometers or first or second order magnetic gradiometers. Detectors 24 could be SQUID magnetometers or gradiometers.

While the invention is discussed above in the context of a MEG system, the invention may be applied to locating other objects oscillating magnetic fields relative to an array of magnetic sensors.

While the mathematical formulae presented herein have been structured to avoid the need for computations using complex numbers, one could perform equivalent calculations using complex numbers at the expense of somewhat greater memory usage and somewhat slower calculation.

Accordingly, the scope of the invention is to be construed in accordance with the substance defined by the following claims.

What is claimed is:

1. A method for locating an object relative to an array of magnetic sensors in an environment in which there is present a noise signal having a fundamental frequency $f_{NOISE}$, the method comprising:

generating one or more magnetic signals by means of one or more magnetic emitters mounted at known locations on the object, the one or more magnetic signals having one or more frequencies;

during an integration time T, detecting the one or more magnetic signals and the noise signal at six or more magnetic detectors; and, determining relative amplitudes of the magnetic signals; wherein the one or more frequencies of the magnetic signals are substantially equal to frequencies at which a power spectrum of the detected noise signal has zeros.

2. A method according to claim 1 wherein the integration time T is equal to $N_1/f_{NOISE}$, where $N_1$ is an integer and $N_1 \geq 2$.

3. A method according to claim 2 wherein the one or more frequencies of the magnetic signals are substantially equal to $N_2/T$ where $N_2$ is an integer which is not an integer multiple of $N_1$.

4. A method according to claim 1 wherein detecting the magnetic signal comprises:

sampling outputs of the six or more magnetic detectors to provide corresponding sequences of samples and, for each of the one or more magnetic detectors;

multiplying each of the samples by a function which varies periodically at a frequency at which the power spectrum of the detected noise signal has a zero; and, summing results of the multiplying.

5. A method according to claim 4 wherein the function is a cosine function.

6. A method according to claim 5 wherein detecting each of the one or more magnetic signals comprises, for each of the one or more magnetic detectors, computing the complex value A given by:

$$A = \left[ \sum_k S_k^m \cos(2\pi k f_q / f_s) - i \sum_k S_k^m \sin(2\pi k f_q / f_s) \right]$$

or a mathematical equivalent thereof where $S_k^m$ is the $k^{th}$ sample from an $m^{th}$ one of the magnetic detectors; k is an index indicating the order of the samples in the sequence of samples from each of the magnetic detectors; $f_q$ is a frequency of the magnetic signal; $f_s$ is a frequency at which the samples are taken; and i is the square root of $-1$.

7. A method according to claim 6 wherein the one or more magnetic signals have frequencies $f_q$ which deviate from frequencies $f_{qi}$ at which the power spectrum of the detected noise signal has zeroes by a deviation amount and the method comprises performing a correction to the complex value A.

8. A method according to claim 1 wherein the one or more magnetic emitters each comprises an electrically conductive coil connected to a source of an alternating electrical current.

9. A method according to claim 8 wherein the one or more magnetic emitters comprise at least three magnetic emitters.

10. A method according to claim 9 comprising operating each of the at least three magnetic emitters to generate a corresponding magnetic signal having a frequency distinct from frequencies of other ones of the magnetic emitters.

11. A method according to claim 9 wherein detecting the magnetic signals at six or more magnetic detectors comprises, for each of the at least three magnetic emitters, detecting the corresponding magnetic signal at each of a first set of magnetic detectors and the method comprises estimating a location of the magnetic emitter based upon relative amplitudes of the corresponding magnetic signal received at a subset of the first set of magnetic detectors which is different from a subset of detectors used for other ones of the at least three magnetic emitters.

12. A method according to claim 1 wherein determining relative amplitudes comprises using one of the magnetic detectors as a reference phase.

13. A method according to claim 12 wherein using one of the magnetic detectors as a reference phase comprises computing:

$$R_q^m = \text{Re}\left( A_q^m \times \frac{|A_q^{m0}|}{A_q^{m0}} \right)$$

or a mathematical equivalent thereof wherein $R_q^m$ is the relative amplitude of the signal from an $q^{th}$ one of the magnetic emitters detected by a $m^{th}$ one of the magnetic detectors; $A_q^m$ is the complex amplitude of the signal from an $q^{th}$ one of the magnetic emitters detected by a $m^{th}$ one of the magnetic detectors; and $A_q^{m0}$ is the complex amplitude of the signal from an $q^{th}$ one of the magnetic emitters detected by a reference one of the magnetic detectors.

14. A method according to claim 1 wherein detecting the magnetic signals at six or more magnetic detectors comprises detecting the magnetic signals at each of a first set of magnetic detectors and the method comprises estimating a location of one of the magnetic emitters based upon relative amplitudes of the corresponding magnetic signal received at a subset of the first set of magnetic detectors.

15. A method according to claim 14 wherein the first set of magnetic detectors includes at least 60 magnetic detectors and the subset of the first set of magnetic detectors includes not more than 50 magnetic detectors.

16. A method according to claim 14 wherein the first set of magnetic detectors includes at least 150 magnetic detectors and the subset of the first set of magnetic detectors includes not more than 50 magnetic detectors.

17. A method according to claim 14 comprising selecting at a first group of magnetic detectors for inclusion in the subset based on an indicator of a variation in the magnetic signal with position of the magnetic emitter.

18. A method according to claim 17 comprising selecting a second group of magnetic detectors for inclusion in the subset based upon a relative amplitude of the magnetic signal detected at the other magnetic detectors.

19. A method according to claim 14 comprising selecting a first group of the magnetic detectors for inclusion in the subset based on a first criterion and selecting a second group of the magnetic detectors for inclusion in the subset based on a second criterion distinct from the first criterion.

20. A method according to claim 19 wherein the first criterion selects for largest relative amplitude of the magnetic signal.

21. A method according to claim 20 wherein the second group selects for large variation in the magnetic signal with position of the magnetic emitter.

22. A method according to claim 21 wherein the first group is larger than the second group.

23. A method according to claim 14 wherein the subset includes 16 or fewer magnetic detectors.

24. A method according to claim 21 wherein the second criterion is based in part upon proximity to a reference magnetic detector.

25. A method according to claim 21 wherein the second criterion comprises selecting magnetic detectors having relatively large values of V given by:

$$V = \frac{|s_m - s_{\max}|}{|\vec{r}_m - \vec{r}_{\max}|}$$

or a substantial mathematical equivalent thereof where $s_{max}$ is the amplitude of the signal at the magnetic detector having the largest signal from the magnetic emitter and $\vec{r}_{max}$ is the location of the magnetic detector having the largest signal from the magnetic emitter.

26. A method according to claim 7 wherein the one or more magnetic emitters comprise at least two magnetic emitters for generating at least two magnetic signals having frequencies $f_q$ which deviate from frequencies $f_{qi}$ at which the power spectrum of the detected noise signal has zeroes by at least two deviation amounts, and wherein performing the correction comprises calculating at least two corrected amplitudes, each of the at least two corrected amplitudes comprising a sum of a correction function applied to the at least two relative amplitudes.

27. A method according to claim 1 wherein the one or more magnetic emitters comprise at least two magnetic emitters for generating at least two magnetic signals having frequencies $f_q$ which deviate from frequencies $f_{qi}$ at which the power spectrum of the detected noise signal has zeroes by at least two deviation amounts, and the method comprises correcting at least two relative amplitudes of the magnetic signals.

28. A method according to claim 27 wherein correcting the relative amplitudes of the magnetic signals comprises calculating at least two corrected amplitudes, each of the at least two corrected amplitudes comprising a sum of a correction function applied to the at least two relative amplitudes.

29. A method according to claim 28 wherein the correction function comprises a function of $f_q$ and $f_{qi}$.

30. A method according to claim 29 wherein the correction function comprises a real correction function and an imaginary correction function.

31. A method according to claim 30 wherein the interval extends from $-T/2$ to $T/2$ and the real correction function comprises:

$$G_C(f_q, f_{qi}) = \frac{2}{T} \int_{-\frac{T}{2}}^{\frac{T}{2}} \cos(2\pi f_q t) e^{-i2\pi f_{qi} t} dt$$

$$= \frac{\sin(\pi(f_q - f_{qi})T)}{\pi(f_q - f_{qi})T} + \frac{\sin(\pi(f_q + f_{qi})T)}{\pi(f_q + f_{qi})T}$$

and the imaginary correction function comprises:

$$G_S(f_q, f_{qi}) = -\frac{2i}{T} \int_{-\frac{T}{2}}^{\frac{T}{2}} \sin(2\pi f_q t) e^{-i2\pi f_{qi} t} dt$$

$$= \frac{\sin(\pi(f_q - f_{qi})T)}{\pi(f_q - f_{qi})T} - \frac{\sin(\pi(f_q + f_{qi})T)}{\pi(f_q + f_{qi})T}.$$

32. A method according to claim 31 wherein the at least two magnetic emitters comprise three magnetic emitters for generating frequencies $f_1$, $f_2$ and $f_3$ which respectively deviate from frequencies $f_{1i}$, $f_{2i}$ and $f_{3i}$ at which the power spectrum of the detected noise signal has zeroes by first, second and third deviation amounts, and wherein calculating the corrected amplitudes from the relative amplitudes is accomplished by matrix equations:

$$\begin{bmatrix} C_1 \\ C_2 \\ C_3 \end{bmatrix} = \begin{bmatrix} G_C(f_1, f_{1i}) & G_C(f_2, f_{1i}) & G_C(f_3, f_{1i}) \\ G_C(f_1, f_{2i}) & G_C(f_2, f_{2i}) & G_C(f_3, f_{2i}) \\ G_C(f_1, f_{3i}) & G_C(f_2, f_{3i}) & G_C(f_3, f_{3i}) \end{bmatrix} \times \begin{bmatrix} R_1 \\ R_2 \\ R_3 \end{bmatrix}$$

and $$\begin{bmatrix} S_1 \\ S_2 \\ S_3 \end{bmatrix} = \begin{bmatrix} G_S(f_1, f_{1i}) & G_S(f_2, f_{1i}) & G_S(f_3, f_{1i}) \\ G_S(f_1, f_{2i}) & G_S(f_2, f_{2i}) & G_S(f_3, f_{2i}) \\ G_S(f_1, f_{3i}) & G_S(f_2, f_{3i}) & G_S(f_3, f_{3i}) \end{bmatrix} \times \begin{bmatrix} I_1 \\ I_2 \\ I_3 \end{bmatrix}$$

where $R_1$, $R_2$, $R_3$ and $I_1$, $I_2$, $I_3$ respectively comprise real and imaginary parts of the relative amplitudes and $C_1$, $C_2$, $C_3$ and $S_1$, $S_2$, $S_3$ respectively comprise real and imaginary parts of the corrected amplitudes.

33. A method according to claim 28 where the integration time is an interval $t_0 \leq t \leq t_0 + T$ and the correction functions are:

$$G_C(f_q, f_{qi}) = \frac{2}{T} \int_{t_0}^{t_0+T} \cos(2\pi f_q t) e^{-i2\pi f_{qi} t} dt$$

$$= G_C^R(f_q, f_{qi}) + G_C^I(f_q, f_{qi})$$

$$G_S(f_q, f_{qi}) = \frac{2i}{T} \int_{t_0}^{t_0+T} \sin(2\pi f_q t) e^{-2\pi f_{qi} t} dt$$

$$= G_S^R(f_q, f_{qi}) + G_S^I(f_q, f_{qi})$$

and the matrix equation relating the real and imaginary amplitudes of the coil signals ($R_p$ and $I_p$) to the real and imaginary signals measured at the ideal frequencies ($C_p$ and $S_p$) is:

$$\begin{bmatrix} C_1 \\ C_2 \\ C_3 \\ S_1 \\ S_2 \\ S_3 \end{bmatrix} = \begin{bmatrix} G_C^R(f_1,f_{1i}) & G_C^R(f_2,f_{1i}) & G_C^R(f_3,f_{1i}) & -G_S^I(f_1,f_{1i}) & -G_S^I(f_2,f_{1i}) & -G_S^I(f_3,f_{1i}) \\ G_C^R(f_1,f_{2i}) & G_C^R(f_2,f_{2i}) & G_C^R(f_3,f_{2i}) & -G_S^I(f_1,f_{2i}) & -G_S^I(f_2,f_{2i}) & -G_S^I(f_3,f_{2i}) \\ G_C^R(f_1,f_{3i}) & G_C^R(f_2,f_{3i}) & G_C^R(f_3,f_{3i}) & -G_S^I(f_1,f_{3i}) & -G_S^I(f_2,f_{3i}) & -G_S^I(f_3,f_{3i}) \\ G_C^I(f_1,f_{1i}) & G_C^I(f_2,f_{1i}) & G_C^I(f_3,f_{1i}) & G_S^R(f_1,f_{1i}) & G_S^R(f_2,f_{1i}) & G_S^R(f_3,f_{1i}) \\ G_C^I(f_1,f_{2i}) & G_C^I(f_2,f_{2i}) & G_C^I(f_3,f_{2i}) & G_S^R(f_1,f_{2i}) & G_S^R(f_2,f_{2i}) & G_S^R(f_3,f_{2i}) \\ G_C^I(f_1,f_{3i}) & G_C^I(f_2,f_{3i}) & G_C^I(f_3,f_{3i}) & G_S^R(f_1,f_{3i}) & G_S^R(f_2,f_{3i}) & G_S^R(f_3,f_{3i}) \end{bmatrix} \times \begin{bmatrix} R_1 \\ R_2 \\ R_3 \\ I_1 \\ I_2 \\ I_3 \end{bmatrix}.$$

34. A method according to claim 28 wherein calculating the corrected amplitude comprises using a 3×3 matrix of complex numbers.

35. A method according to claim 31 wherein calculating the corrected amplitudes comprises using a 3×3 matrix of complex numbers.

36. A method according to claim 1 comprising determining positions of the magnetic emitters from the relative amplitudes of the magnetic signals.

37. A method according to claim 36 comprising comparing the positions of the magnetic emitters to corresponding reference positions and triggering an alarm unless distances between the magnetic emitters and the corresponding reference positions are less than a threshold.

38. A method according to claim 36 comprising comparing the positions of the magnetic emitters to corresponding reference positions and generating a sensory feedback indicator based upon departures of the positions of the magnetic emitters from the corresponding reference positions.

* * * * *